United States Patent
Minato et al.

(10) Patent No.: US 6,648,867 B2
(45) Date of Patent: Nov. 18, 2003

(54) DISPOSABLE DIAPER WITH BREATHABLE AND LIQUID-RESISTANT SIDE FLAPS

(75) Inventors: Hironao Minato, Kagawa-ken (JP); Yasushi Sayama, Kagawa-ken (JP); Naomi Suzuki, Kagawa-ken (JP); Rumiko Shiraishi, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 266 days.

(21) Appl. No.: 09/726,862

(22) Filed: Nov. 30, 2000

(65) Prior Publication Data
US 2001/0039409 A1 Nov. 8, 2001

(30) Foreign Application Priority Data
Nov. 30, 1999 (JP) .......................................... 11-339284

(51) Int. Cl.[7] ................................................ A61F 13/15
(52) U.S. Cl. ............................ 604/385.04; 604/385.28
(58) Field of Search ...................... 604/385.01, 385.04, 604/385.28

(56) References Cited

U.S. PATENT DOCUMENTS

| | | | | |
|---|---|---|---|---|
| 4,347,844 A | * | 9/1982 | Ohki et al. ................. | 128/287 |
| 4,425,128 A | * | 1/1984 | Motomura ................... | 604/381 |
| 5,167,653 A | * | 12/1992 | Igaue et al. .............. | 604/385.2 |
| 5,451,217 A | * | 9/1995 | Fujioka et al. .............. | 604/378 |
| 5,624,424 A | * | 4/1997 | Saisaka et al. ........... | 604/385.2 |
| 5,849,001 A | * | 12/1998 | Torimae et al. ............. | 604/372 |

FOREIGN PATENT DOCUMENTS

| | | |
|---|---|---|
| JP | A 8-289902 | 11/1996 |
| JP | A 8-322876 | 12/1996 |

\* cited by examiner

*Primary Examiner*—Weilun Lo
*Assistant Examiner*—Michael G. Bogart
(74) *Attorney, Agent, or Firm*—Butzel Long (57) ABSTRACT

A disposable diaper is provided with a pair of side flaps lying transversely outside the associated side edge of an absorbent core, and the side flaps is formed by a first side sheet connected to the associated side edge portion of a topsheet lying in the vicinity of the associated side edge of the core and extending longitudinally of the diaper and a second side sheet connected to the associated side edge portion of the topsheet and the associated side edge portion of a backsheet both lying in the vicinity of the associated side edge of the core wherein both the first and second side sheets have a water pressure resistance of 100~1500 mm and a breathing resistance of 0.03~0.8 Kpa·s/m.

3 Claims, 4 Drawing Sheets

DISPOSABLE DIAPER WITH BREATHABLE AND LIQUID-RESISTANT SIDE FLAPS

BACKGROUND OF THE INVENTION

This invention relates to a disposable diaper adapted to absorb and contain body fluids discharged thereon.

As one example of disposable diapers, there has already been proposed a disposable diaper comprising a liquid-pervious topsheet, a liquid-impervious backsheet and a liquid-absorbent core disposed between these two sheets, and the diaper further includes a pair of side flaps lying outside transversely opposite side edges of the core and longitudinally of the diaper and a pair of leak-barrier cuffs lying in the vicinity of the transversely opposite side edges of the core and normally biased to rise on the inner surface of the diaper. Each of the side flaps is formed by the associated side edge portion of the backsheet lying transversely outside the associated side edge of the core and extending longitudinally of the diaper and the associated outer side edge portion of the cuff lying transversely outside its fixed side edge portion. In the side flap, the side edge portion of the topsheet terminates immediately outside the associated side edge of the core while the associated side edge portions of the backsheet and the cuff, respectively, extend transversely outward beyond the associated side edge portion of the topsheet. The disposable diaper of such type is disclosed, for example, in Japanese Patent Application Disclosure Nos. 1996-289902 and 1996-322876.

The side flaps and the leak-barrier cuffs surround a wearer's legs and partially occupy a crotch region of the wearer being prone to excretion leak and stuffiness. To avoid these problems, it is desired to improve both the water resistance and the breathability of the side flaps and the cuffs.

If a plastic film is used as a stock material for the backsheet, a relatively high water resistance can be obtained but it is impossible to obtain a desired breathability. Even if the plastic film is processed to have fine pores, it is impossible to obtain a breathability sufficient to prevent the interior of the diaper from becoming stuffy.

In the case of the backsheet and the cuffs both formed by a nonwoven fabric, an effort to improve the water resistance by increasing the basis weight of the synthetic resin fiber forming the nonwoven fabric will result in increasing the fiber density in the nonwoven fabric and correspondingly deteriorate the breathability. On the contrary, an effort to improve the breathability by reducing the basis weight of the fiber forming the nonwoven fabric will reduce the fiber density in the nonwoven fabric and correspondingly deteriorate the water resistance.

SUMMARY OF THE INVENTION

It is an object of this invention to provide a disposable diaper provided with a pair of side flaps and a pair of leak-proof cuffs presenting optimized water pressure resistance and breathing resistance so that both a sufficiently high water resistance and a sufficiently high breathability can be ensured in the side flaps and the cuffs.

According to this invention, there is provided a disposable diaper comprising a liquid-pervious topsheet, a liquid-impervious backsheet and a liquid-absorbent core disposed therebetween, and formed with a pair of side flaps lying outside transversely opposite side edges of the core and extending longitudinally of the diaper, wherein: each of the side flaps is formed by a breathable and liquid-resistant first side sheet connected to the associated side edge portion of the topsheet lying in the vicinity of the associated side edge of the core and extending longitudinally of the diaper and at least one breathable and liquid-resistant second side sheet connected to the associated side edge portions of the top- and backsheets both lying in the vicinity of said associated side edge of the core or at least to the associated side edge portion of the backsheet and extending longitudinally of the diaper under the first side sheet wherein both the first and second side sheets have a water pressure resistance of 100~1500 mm and a breathing resistance of 0.03~0.8 Kpa·s/m.

With the disposable diaper according to this invention, each of the side flaps is formed by the first and second side sheets presenting a water pressure resistance of 100~1500 mm and a breathing resistance of 0.03~0.8 Kpa·s/m. Adjustment of these resistance values in such ranges, respectively, ensures the side flap to present a sufficiently high water pressure resistance as well as a sufficiently high breathability. As a result, leak of excretion otherwise occurring through the side flap can be reliably avoided and moisture generated within the diaper can be reliably breathed out to the exterior and thereby to avoid undesirable stuffiness otherwise generated within the diaper.

With the diaper 1 implemented to have the pair of leak-proof cuffs, it is ensured that these cuffs prevent a sufficiently high water pressure resistant as well as a sufficiently high breathability so far as the breathing resistance of the first side sheet is adjusted within a range of 0.03~0.8 Kpa·s/m. In this way, the diaper can prevent excretion discharged thereon from leaking through the cuffs and breath out moisture to the exterior through the cuffs to avoid undesirable stiffness otherwise generated within the diaper. Furthermore, adjustment of the water pressure resistance of the first side sheet to be higher than that of the second side sheet(s) effectively prevent exudation of excretion otherwise occurring through the first side sheet toward the second sheet(s).

The side flap comprising the first side sheet and two or more second side sheets is more effective than the side flap comprising the first side sheet and a single side sheet to improve its water pressure resistance and the diaper including such side flap is suitable particularly as the diaper exclusively used by adult discharging a relatively large amount of excretion.

DETAILED DESCRIPTION OF THE PREFERRED EMBODIMENTS

Details of a disposable diaper according to this invention will be more fully understood from the description given hereunder with reference to the accompanying drawings.

Figure 1:
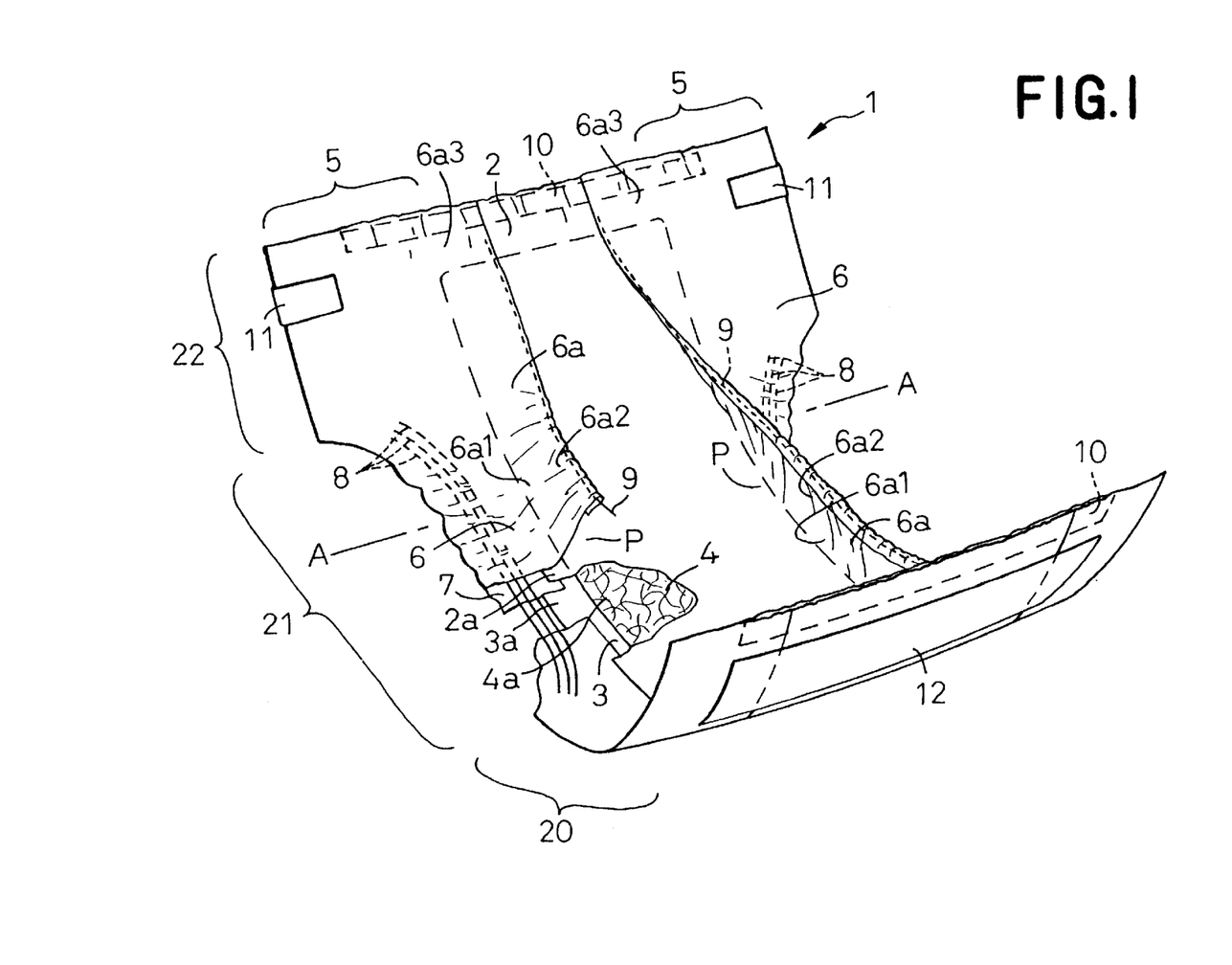
FIG. 1 is a perspective view showing one embodiment of a partially cutaway disposable diaper according to this invention.
Figure 2:
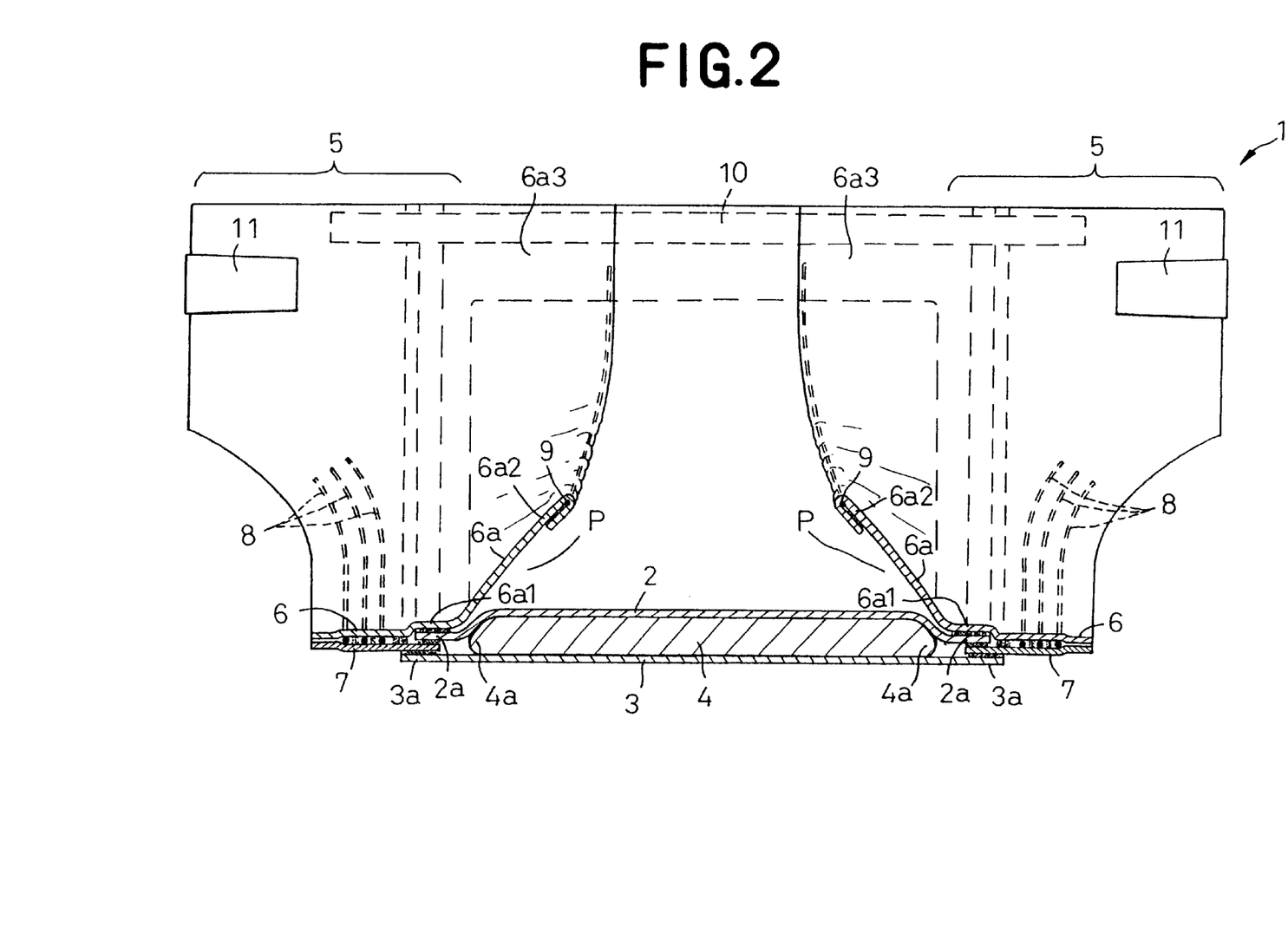
FIG. 2 is a sectional view taken along line A—A in FIG. 1.

FIG. 1 is a perspective view showing one embodiment of a partially cutaway disposable diaper according to this invention and FIG. 2 is a sectional view taken along line A—A in FIG. 1. A diaper 1 basically comprises a liquid-pervious topsheet 2, a liquid-impervious backsheet 3 and a liquid-absorbent core 4 disposed between the top- and backsheets 2, 3 and bonded to the inner surface of at least one of these two sheets 2, 3. Configurationally, the diaper 1 has a front waist region 20, a rear waist region 22 and a crotch region 21 extending between these front and rear waist regions 20, 22 as viewed longitudinally of the diaper 1. The diaper 1 further includes a pair of side flaps 5 extending longitudinally of the diaper 1 outside transversely opposite side edges 4a of the core 4 and a pair of leak-barrier cuffs 6a normally biased to rise on the inner surface of the diaper 1.

Each of the side flaps 5 comprises a first side sheet 6 bonded to a side edge portion 2a of the topsheet 2 defined in the vicinity of the side edge 4a of the core 4 and extending longitudinally of the diaper 1, on one hand, and a second side sheet 7 bonded to a side edge portion 3a of the backsheet 3 defined in the vicinity of the side edge 4a of the core 4 and extending longitudinally of the diaper 1, on the other hand. Of the side flap 5, the first side sheet 6 overlies the topsheet 2 and the second sheet 7 underlies the first side sheet 6. Both the first and second side sheets 6, 7 are made of a nonwoven fabric formed by thermoplastic synthetic resin fiber. In the crotch region 21, the side flap 5 has its outer contour laterally curved inwardly of the diaper 1, describing a circular arc, so that the diaper 1 as a whole presents an hourglass-like contour. The side flap 5 is provided between the first and second sheets 6, 7 with a leg-hole's elastically stretchable member 8 secured under tension to the inner surface of at least one of these first and second side sheets 6, 7.

The first side sheet 6 extends inwardly of the diaper 1 from the side edge portion 2a of the topsheet 2 to form each of the leak-barrier cuffs 6a. The leak-proof cuff 6a comprises a fixed side edge portion 6a1 bonded to the upper surface of the topsheet 2 along its side edge portion 2a by means of adhesive and extending longitudinally of the diaper 1, a free side edge portion 6a2 lying inside the fixed side edge portion 6a1 and extending longitudinally of the diaper 1 and longitudinally opposite fixed end portions 6a3 bonded to the upper surface of the topsheet 2 as they are collapsed inwardly of the diaper 1. The free side edge portion 6a2 is provided with an elastically stretchable member 9 extending longitudinally of the diaper 1 and secured under tension thereto so that a portion of the free side edge portion 6a2 may wrap the member 9.

The first and second side sheets 6, 7 respectively have a water pressure resistance of 100~1500 mm and a breathing resistance of 0.03~0.8 Kpa·s/m. It should be understood that the breathing resistance is preferably in a range of 0.05~0.6 Kpa·s/m.

The water pressure resistance of the side sheets may be enhanced, for example, by increasing the basis weight of the synthetic resin fiber forming the nonwoven fabric and by reducing the fiber interstices therein. The breathing resistance may be alleviated, for example, by reducing the basis weight of the nonwoven fabric forming the nonwoven fiber and enlarging the fiber interstices therein. Enhancement of the water pressure resistance and alleviation of the breathing resistance thus conflict with each other. However, it is possible for both the side flaps 5 and the cuffs 6a of the diaper 1 according to the present invention to have sufficiently high water pressure resistance as well as sufficiently high breathability without victimizing any one of the water pressure resistance and the breathability by adjusting the water pressure resistance and the breathing resistance of the first and second side sheets 6, 7 in the ranges as have been described.

The water pressure resistance of the side sheets 6, 7 less than 100 mm would sometimes result in exudation and leakage of excretion through these side sheets 6, 7. The water pressure resistance of the side sheets 6, 7 exceeding 1500 mm, on the other hand, would inevitably increase the basis weight of the fiber forming these side sheets 6, 7 and therefore the fiber density of the nonwoven fabric. The side sheets 6, 7 would have their rigidity correspondingly increased, so the side flaps 5 and the cuffs 6a would give a diaper wearer uncomfortable feeling as these side flaps 5 and cuffs 6a come in contact with the wearer's crotch.

The breathing resistance of the side sheets 6, 7 less than 0.03 Kpa·s/m would reduce the basis weight of the fiber forming the side sheets 6, 7 to a level at which the side sheets 6, 7 have their water pressure resistance unacceptably reduced and are impaired and broken down. On the other hand, the breathing resistance of the side sheets 6, 7 exceeding 0.8 Kpa·s/m would increase the basis weight of the fiber forming the side sheets 6, 7 and correspondingly deteriorate the breathability thereof. As a result, it would be impossible for such diaper 1 to breathe moisture out from the interior of the diaper 1 through the side flaps 5 and the cuffs 6a and to prevent a stuffiness generated inside the diaper 1.

The side flap 5 has its water pressure resistance and breathing resistance substantially twice as high as those of the first and second side sheets 6, 7 since the side flap 5 is formed by these first and second sheets 6, 7 placed upon each other. Concerning the rigidity, this is not true, since it is not apprehended that the rigidity of one of the first and second side sheets 6, 7 might enhance the rigidity of the other although the side flap 5 comprises these first and second side sheets 6, 7 are placed upon each other.

In the side flap 5, side edge portions 2a, 3a of the top- and backsheets 2, 3, respectively, terminate immediately outside the associated side edge 4a of the core 4, and the first and second side sheets 6, 7 extend outward beyond the associated side edge portions 2a, 3a of the top- and backsheets 2, 3, as will be apparent from FIG. 2. The second side sheet 7 is partially disposed between the associated side edge portions 2a, 3a of the top- and backsheets 2, 3, respectively, and bonded to the associated side edge portions 2a, 3a of the top- and backsheets 2, 3. The first and second side sheets 6, 7 are placed upon each other and, in such relative position, have their inner surfaces intermittently bonded to each other by means of adhesive. The cuffs 6a cooperate with the topsheet 2 to form a pair of pockets P opening inward transversely of the diaper 1. An alternative arrangement is also possible such that the second side sheets 7 underlie the backsheet 3 and are partially bonded to the respective side edge portions 3a of the backsheet 3.

The front and rear waist regions 20, 22 of the diaper 1 are respectively provided along longitudinal ends thereof with waist-hole's elastically stretchable film-like members 10 transversely extending between the top- and backsheets 2, 3 and secured under tension to the inner surface of at least one of these top- and backsheets 2, 3. In the rear waist region 22, a pair of tape fasteners 11 extending inward transversely of the diaper 1 have their proximal end portions attached to the side flaps 5, respectively. In the front waist region 20, a rectangular strip of target tape 12 is attached to the surface of the backsheet 3 so that the tape fasteners 11 may be anchored on this strip of target tape 12.

Referring to FIG. 1, the leg-hole's elastic members 8, the waist-hole's elastic members 10 and the elastic members 9 bonded to the cuffs 6a along their free side edge portions 6a2 are relieved of tension to form gathers along the respective longitudinal ends of the front and rear waist regions 20, 22 as well as along the respective free side edge portions 6a2 of the cuffs 6a. As shown, the diaper 1 is curved with its inner surface inside and contraction of the elastic members secured to the respective free side edge portions 6a2 of the cuffs 6a causes the respective free side edge portions 6a2 of the cuffs 6a to rise on the inner surface of the diaper 1.

The diaper 1 is formed with the pair of leg-holes and the waist-hole (not shown) as the respective free side edge portions of the tape fasteners 11 are anchored on the strip of the target tape 12 by means of pressure-sensitive adhesive (not shown) applied on the inner surfaces of the free side edge portions.

Figure 3:
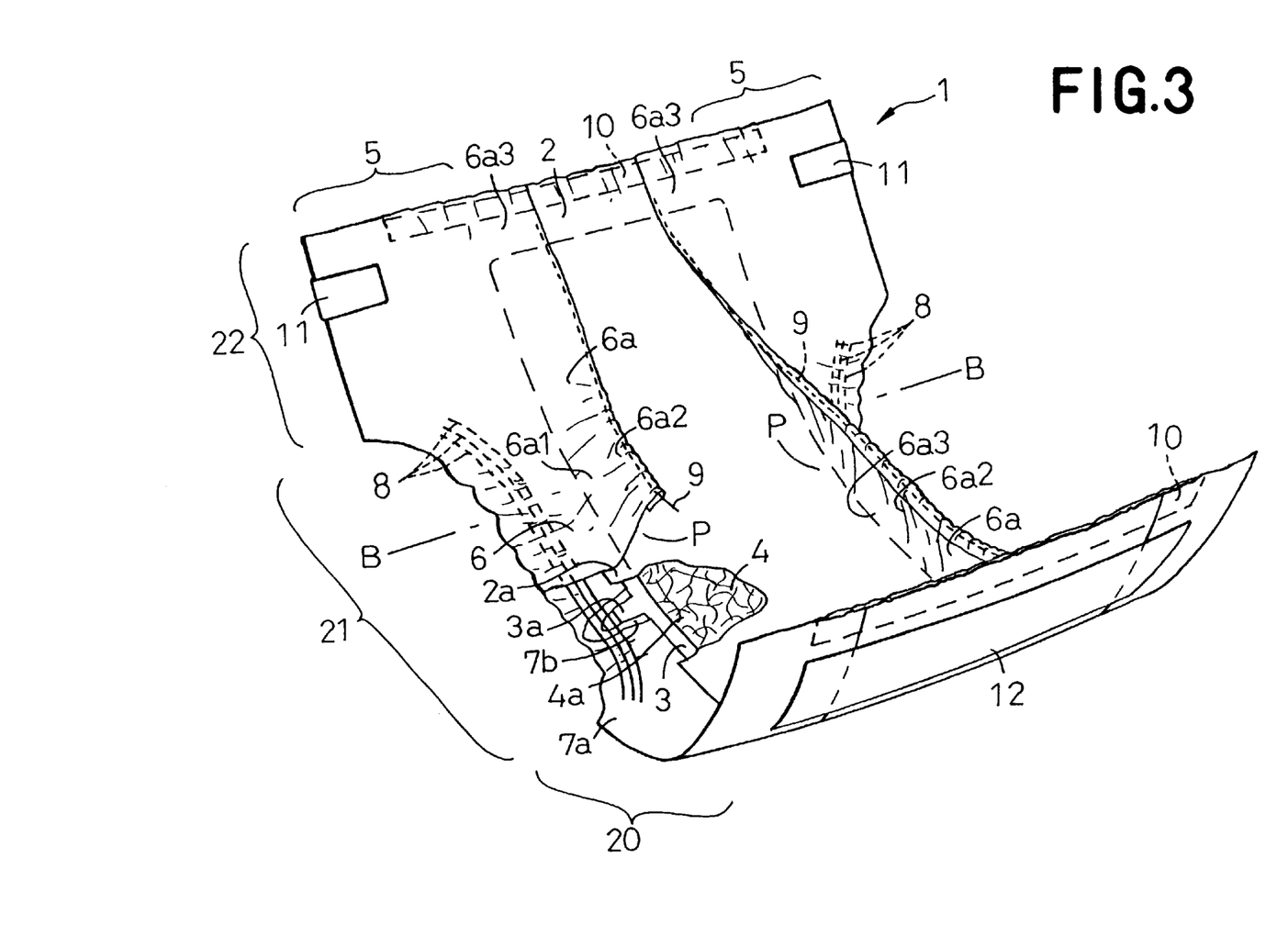
FIG. 3 is a view similar to FIG. 1 showing an alternative embodiment of this invention.
Figure 4:
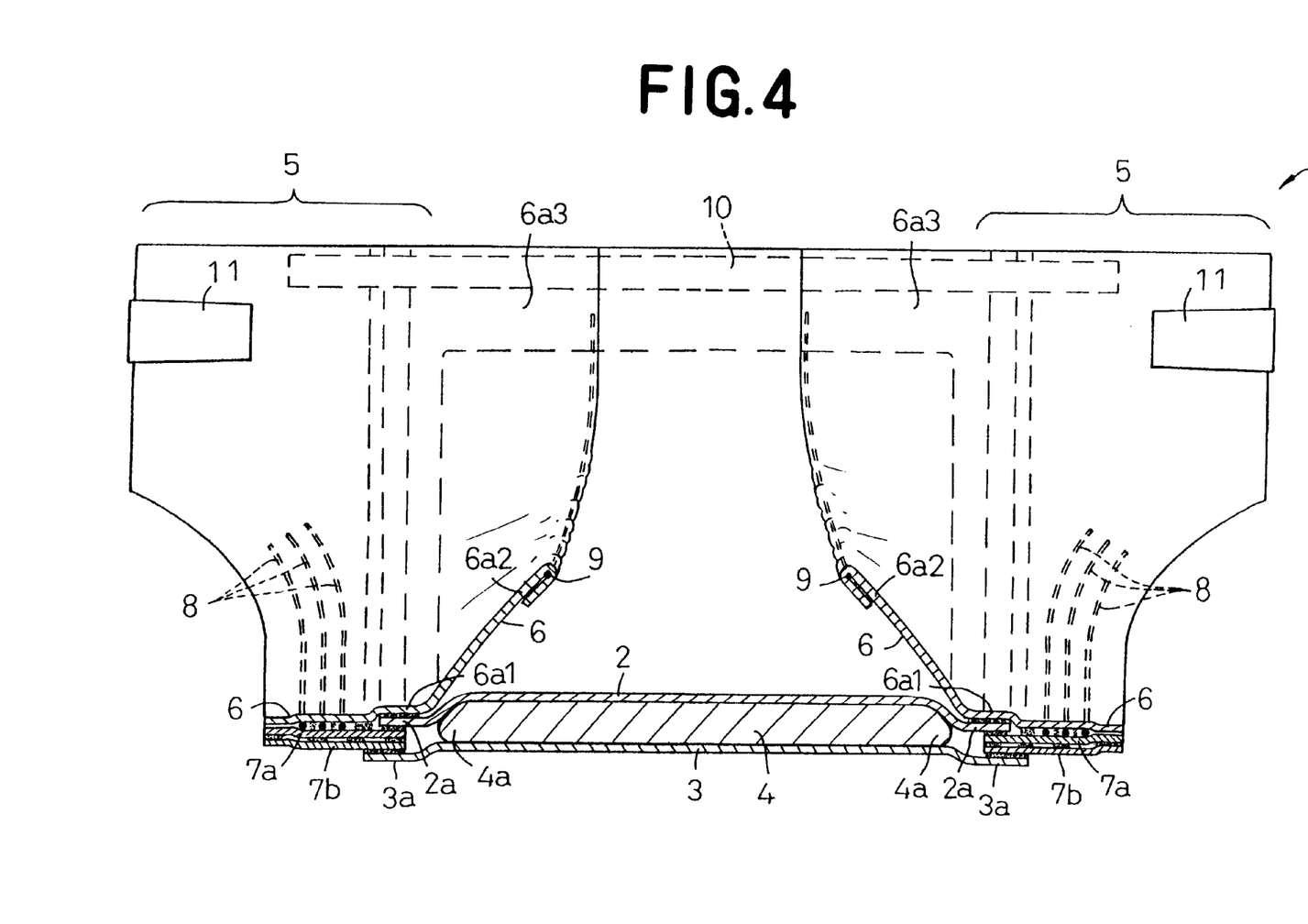
FIG. 4 is a sectional view taken along line B—B in FIG. 3.

FIG. 3 is a view similar to FIG. 1 showing an alternative embodiment of this invention and FIG. 4 is a sectional view taken along line B—B in FIG. 3. This alternative embodiment of the diaper 1 is similar to that shown by FIG. 1 in that the diaper 1 comprises the topsheet 2, the backsheet 3, the core 4 disposed between the top- and backsheets 2, 3, the side flaps 5 lying outside the transversely opposite side edges 4a of the core 4 and extending longitudinally of the diaper 1 and the leak-barrier cuffs 6a normally biased to rise on the inner surface of the diaper 1, configurationally defining the front waist region 20, the rear waist region 22 and the crotch region 21 extending between the front and rear waist regions 20, 22.

In the case of the diaper 1 shown by FIG. 3, the side flap 5 comprises the side sheet 6 bonded to the associated side edge portion 2a of the topsheet 2 and extending longitudinally of the diaper 1 and two second side sheets 7a, 7b bonded to the associated side edge portion 2a of the topsheet 2 and to the associated side edge portion 3a of the backsheet 3, respectively, both extending longitudinally of the diaper 1.

The second side sheets 7a, 7b are placed upon each other and, in such relative position, have their inner surfaces intermittently bonded to each other by means of adhesive. The first side sheet 6 and the second side sheets 7a, 7b respectively have a water pressure resistance of 100~1500 mm and a breathing resistance of 0.03~0.8 Kpa·s/m. It should be understood that the breathing resistance is preferably in a range of 0.05~0.6 Kpa·s/m.

According to this alternative embodiment of the diaper 1, the side flap 5 has its water pressure resistance and breathing resistance substantially treble as high as those of the first and second side sheets 6, 7a, 7b since the side flap 5 is formed by these first and second sheets 6, 7a, 7b placed one upon another. Compared to the previous embodiment of the diaper 1 in which the side flap 5 comprises the first side sheet 6 and the single second side sheet 7, the side flap 5 in this alternative embodiment presents an improved water pressure resistance somewhat victimizing its breathability. Accordingly, the diaper 1 adopting this alternative embodiment of the side flaps 5 is suitable as the diaper exclusively used for adult discharging a relatively large amount of excretion. In this embodiment also, it is not apprehended that the rigidity of one of the second side sheets 7a, 7b might enhance the rigidity of the other and consequently the rigidity of the side flap 5 as a whole might become treble as high as those of the respective sheets 6, 7a, 7b although these second side sheets 7a, 7b are placed upon each other.

As will be apparent from FIG. 4, the side edge portions 2a, 3a of the top- and backsheets 2, 3, respectively, terminate immediately outside the associated side edge 4a of the core 4, and the first and second side sheets 6, 7a, 7b extend outward beyond the associated side edge portions 2a, 3a of the top- and backsheets 2, 3. The second side sheets 7a, 7b are disposed between the associated side edge portions 2a, 3a of the top- and backsheets 2, 3, respectively, and the second sheet 7a is bonded to the topsheet 2 by means of adhesive while the second sheet 7b is bonded to the backsheet 3 by means of adhesive. The first and second side sheets 6, 7a, 7b are placed one upon another and, in such relative position, have their inner surfaces intermittently bonded one to another by means of adhesive.

This invention may be implemented also in a manner that the diaper 1 has no leak-barrier cuffs 6a. In this case, the first side sheet 6 no more extends inward beyond the associated side edge portion 2a of the topsheet 2 transversely of the diaper 1 but may terminate at the associated side edge portion 2a of the topsheet 2 and the portion of the first side sheet 6 overlying or underlying the associated side edge portion 2a of the topsheet 2 is bonded to the upper or lower surface of the topsheet 2. It is also possible to form the side flap 5 by three or more second side sheets placed upon the first side sheet 6.

The water pressure resistance presented by the first side sheet 6 and the second side sheets 7, 7a, 7b is preferably adjusted to be in a relationship of the first side sheet>the second sheets. Of excretion, feces contains a relatively large amount of organic substances such as protein and lipid and therefore presents a relatively low surface tension on the nonwoven fabric. If the fiber forming this nonwoven fabric is polyolefine resin, an affinity between the organic substances in feces and the polyolefine resin facilitates feces to permeate the nonwoven fabric. With the diaper 1 according to this invention, the water pressure resistance of the first side sheet 6 may be adjusted to be higher than those of the second side sheets 7, 7a, 7b as has been described above not only to avoid undesirable exudation of feces from the cuff 6a toward the side flap 5 but also to avoid undesirable exudation of feces from the first side sheet 6 toward the second side sheets 7, 7a, 7b.

The inventors measured the breathing resistance presented by the first side sheet 6 and the second sheets 7, 7a, 7b using Model KES-F8 of KATO TECH Co., Ltd. Measurement of the breathing resistance was conducted five times for each sample and average values of these five measurements were obtained as the breathing resistance of the first side sheet 6 and the second side sheets 7, 7a, 7b.

The topsheet 2 may be formed by a liquid-pervious nonwoven fabric or porous plastic film, preferably by a liquid-pervious hydrophilic sheet. The backsheet 3 may be formed by plastic film or a laminated sheet consisting of a hydrophobic nonwoven fabric and a plastic film.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. In addition, an SMS nonwoven fabric may be also useful, which comprises a melt blown nonwoven fabric having a high water resistance sandwiched between two layers of a spun bond nonwoven fabric each having high strength and softness. The SMS nonwoven fabric may be made by steps of sandwiching the melt blown nonwoven fabric between the two layers of spun bond nonwoven fabric and then bonding these melt blown nonwoven fabric and spun bond nonwoven fabric using a press technique. As component fiber of the nonwoven fabric, there are available polyolefine, polyester and polyamide fibers and conjugated fiber of polyethylene/polypropylene or polyester and the like.

The core 4 comprises a mixture of fluff pulp and highly absorptive polymer grains compressed to a desired thickness and entirely covered with a water-pervious sheet (not shown) such as tissue paper. Bonding of the core 4, the elastic members 8, 9, 10 and the sheets 2, 3, 6, 7, 7a, 7b may be carried out using suitable adhesive such as hot melt adhesive or pressure-sensitive adhesive or a heat-sealing technique.

What is claimed is:

1. A disposable diaper comprising:
   a liquid-pervious topsheet;
   a liquid-impervious backsheet;
   a liquid-absorbent core disposed disposed between the liquid-pervious topsheet and the liquid-impervious backsheet: and
   a pair of side flaps lying outside transversely opposite side edges of said liquid-absorbent core and extending longitudinally of the diaper,
   each of said pair of side flaps being formed from:
      a breathable and liquid-resistant first side sheet connected to a side edge portion of said liquid-previous topsheet and lying in a vicinity of a side edge of said liquid-absorbent core and extending longitudinally of the diaper; and
      at east one breathable and liquid-resistant second side sheet connected to at least one of side edge portions of said liquid-pervious topsheet and liquid-impervious backsheet in a vicinity of said side edge of said liquid-absorbent core, or to at least to a side edge portion of said liquid-impervious backsheet and extending longitudinally of the diaper under said first side sheets both said first and second side sheets having a water pressure resistance of 100~1500 mm and a breathing resistance of 0.03~0.8 Kpa·s/m.

2. The disposable diaper according to claim 1, wherein each first side sheet forms a leak-barrier cuff overlying said liquid-pervious topsheet and extending inward from a side edge portion of said liquid-pervious topsheet transversely of the diaper, said leak-barrier cuff being normally biased to rise on an inner surface of said diaper,
   said leak-barrier cuff having a fixed side edge portion bonded to the side edge portion of said liquid-pervious topsheet, a free side edge portion lying transversely inside said fixed side edge portion and extending longitudinally of the diaper, and longitudinally opposite end portions bonded to longitudinally opposite ends of the diaper, said free side edge portion being elastically stretchable longitudinally of the diaper.

3. The disposable diaper according to claim 1, wherein said first and second side sheets comprise a nonwoven fabric made of thermoplastic synthetic resin fiber and said first side sheet has a water pressure resistance higher than that of said second side sheet.

* * * * *

(12) EX PARTE REEXAMINATION CERTIFICATE (5452nd)
United States Patent
Minato et al.

(10) Number: US 6,648,867 C1
(45) Certificate Issued: Jul. 11, 2006

(54) DISPOSABLE DIAPER WITH BREATHABLE AND LIQUID-RESISTANT SIDE FLAPS

(75) Inventors: Hironao Minato, Kagawa-ken (JP); Yasushi Sayama, Kagawa-ken (JP); Naomi Suzuki, Kagawa-ken (JP); Rumiko Shiraishi, Kagawa-ken (JP)

(73) Assignee: Uni-Charm Corporation, Kawanoe (JP)

Reexamination Request:
No. 90/007,430, Feb. 22, 2005

Reexamination Certificate for:
Patent No.: 6,648,867
Issued: Nov. 18, 2003
Appl. No.: 09/726,862
Filed: Nov. 30, 2000

(30) Foreign Application Priority Data

Nov. 30, 1999 (JP) ............................................. 11-339284

(51) Int. Cl.
*A61F 13/15* (2006.01)

(52) U.S. Cl. .............................. 604/385.04; 604/385.28
(58) Field of Classification Search ............ 604/385.04, 604/385.01, 385.28
See application file for complete search history.

(56) References Cited

U.S. PATENT DOCUMENTS

| | | | |
|---|---|---|---|
| 4,347,844 A | * | 9/1982 | Ohki et al. .................. 604/368 |
| 4,425,128 A | * | 1/1984 | Motomura .................. 604/381 |
| 4,900,317 A | | 2/1990 | Buell |
| 5,080,658 A | * | 1/1992 | Igaue et al. ............ 604/385.27 |
| 5,167,653 A | * | 12/1992 | Igaue et al. ............ 604/385.04 |
| 5,451,217 A | * | 9/1995 | Fujioka et al. ............... 604/378 |
| 5,624,424 A | * | 4/1997 | Saisaka et al. ......... 604/385.28 |
| 5,849,001 A | * | 12/1998 | Torimae et al. ............. 604/372 |

FOREIGN PATENT DOCUMENTS

| | | | |
|---|---|---|---|
| EP | 0329160 | | 2/1989 |
| JP | 8289902 A | * | 11/1996 |
| JP | 8322876 A | * | 12/1996 |

OTHER PUBLICATIONS

Copy of European Search Report for EP 00 31 0575.

* cited by examiner

*Primary Examiner*—Michael O'Neill (57) ABSTRACT

A disposable diaper is provided with a pair of side flaps lying transversely outside the associated side edge of an absorbent core, and the side flaps is formed by a first side sheet connected to the associated side edge portion of a topsheet lying in the vicinity of the associated side edge of the core and extending longitudinally of the diaper and a second side sheet connected to the associated side edge portion of the topsheet and the associated side edge portion of a backsheet both lying in the vicinity of the associated side edge of the core wherein both the first and second side sheets have a water pressure resistance of 100–1500 mm and a breathing resistance of 0.03–0.8 Kpa·s/m.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–3 is confirmed.

* * * * *